(12) United States Patent
Zarecky et al.

(10) Patent No.: US 12,078,288 B2
(45) Date of Patent: Sep. 3, 2024

(54) MOUNTING ASSEMBLY

(71) Applicant: National Creative Enterprises, Inc., Savage, MN (US)

(72) Inventors: Joshua George Zarecky, Fishers, IN (US); Michael Samuel Sabatino, Greenwood, IN (US)

(73) Assignee: NATIONAL CREATIVE ENTERPRISES, INC., Burnsville, MN (US)

( * ) Notice: Subject to any disclaimer, the term of this patent is extended or adjusted under 35 U.S.C. 154(b) by 0 days.

(21) Appl. No.: 17/966,261

(22) Filed: Oct. 14, 2022

(65) Prior Publication Data

US 2024/0125427 A1 Apr. 18, 2024

(51) Int. Cl.
*F16M 13/02* (2006.01)
*B67D 3/00* (2006.01)

(52) U.S. Cl.
CPC ........... *F16M 13/02* (2013.01); *B67D 3/0029* (2013.01)

(58) Field of Classification Search
CPC .... F16M 13/02; F16M 13/022; A47B 73/004; B67D 3/0029; F16C 13/084
USPC ....... 248/686, 689, 691, 102, 103, 104, 105, 248/106, 311.2, 312, 312.1; 211/75.211, 211/63, 66, 88.01, 85.19–85.23
See application file for complete search history.

(56) References Cited

U.S. PATENT DOCUMENTS

| | | | | |
|---|---|---|---|---|
| 3,603,550 A * | 9/1971 | Byrd | ...................... | A62C 13/78 248/154 |
| 5,361,927 A * | 11/1994 | Frei | ........................... | E05F 5/00 220/827 |
| 5,881,935 A * | 3/1999 | Ono | ........................ | B60N 3/102 220/531 |
| 7,922,246 B2 * | 4/2011 | Gale | ....................... | B60R 11/00 297/188.06 |
| 8,011,634 B1 * | 9/2011 | Johnson | ................... | A61G 5/10 224/434 |
| 8,220,764 B2 * | 7/2012 | Ziaylek | .................. | A62B 25/00 248/316.1 |
| 9,764,171 B2 * | 9/2017 | Ziaylek | .................. | A62B 25/00 |
| 9,814,914 B2 * | 11/2017 | Ziaylek | ................. | F16F 7/1017 |
| 11,001,206 B1 | 5/2021 | Zarecky | | |
| 11,007,951 B1 | 5/2021 | Zarecky | | |
| 2022/0136291 A1 * | 5/2022 | Sun | ......................... | E05B 81/18 49/280 |

* cited by examiner

*Primary Examiner* — Alfred J Wujciak
(74) *Attorney, Agent, or Firm* — Brad J. Thorson; DeWitt LLP

(57) ABSTRACT

Mounting a device to a surface is achieved using a mount coupled to the surface and including a swing arm hinged so that the swing arm is movable between an open position permitting insertion or removal of the device, and a capture position in which the swing arm holds the device. Ideally, hinges include a retainer such as a torque insert are a part of the mount.

10 Claims, 7 Drawing Sheets

MOUNTING ASSEMBLY

CROSS-REFERENCED TO RELATED APPLICATIONS

Not applicable

STATEMENT REGARDING FEDERALLY SPONSORED RESEARCH OR DEVELOPMENT

Not applicable

BACKGROUND OF THE INVENTION

I. Field of the Invention

The present invention relates to equipment mounting systems, and more specifically to mounts for containers holding medical equipment to ensure the containers are adequately supported by a surface, e.g., a wall of a building or a surface of a transport vehicle such as a cart or ambulance.

II. Discussion of the Prior Art

Medical equipment tends to be very expensive and can become damaged by a fall. For example, any time medical equipment is transported via a transport vehicle, precautions must be taken to secure the equipment. This is necessary to prevent damage to the equipment and to prevent the equipment from falling and causing injury.

As explained in U.S. Pat. No. 11,007,951, fully incorporated herein by reference, medical equipment such as ultrasound equipment, patient monitors and cardiac defibrillators are quite heavy and very expensive. Often, medical equipment for an ambulance is designed to be stored in a container such as hard or soft case, duffel, or backpack. This makes it easier for paramedics or others to transport the equipment from the ambulance to the location of the injured or ill person to be treated. While in the ambulance, the case, duffel, or backpack must be secured in place. A mount used to do so should be durable, simple, and intuitive to operate, and provide secure retention of a case, duffel, or backpack. Such a mount should also have a reliable securement mechanism with minimal moving parts, and be designed to make loading the case, duffel or backpack into the mount, or removing the case, duffel or backpack from the mount, relatively easy. The mount should also provide for one-handed operation.

A need therefore exists for a mount that meets all the design objectives, and address each of the problems, discussed above.

SUMMARY OF THE INVENTION

The foregoing design objectives are met, and the foregoing problems are solved, by a mount comprising a bracket and a swing arm adapted to be coupled to the bracket by a pair of hinge assemblies. The bracket includes a mounting plate having a top section, a center section, and a bottom section. Extending outwardly from the top section is a top plate. A pair of arms extend from the center section. Each arm comprises a laterally extending plate, and an outwardly projecting hinge mount plate. Extending outwardly from the bottom section is a bottom plate. Capture plates extend upwardly from each of three free edges of the bottom plate, i.e., a front free edge and a pair of opposing side free edges, at an angle greater than 90 degrees from the bottom plate, e.g., 120 degrees for each of the capture plates extending from the free side edges and 112 degrees for the capture plate extending from the front free edge. The bracket may be formed as a single piece of mold plastic or bent metal.

The swing arm is generally u-shaped having two parallel legs and a connecting section from which the two legs extend. The connecting section may be formed as a continuous curve or may comprise a series of flat subsections angled with respect to each other. The entire swing arm may be formed as a single piece of molded plastic or bent metal.

The hinge assemblies are employed to rotatably couple the parallel legs of the swing arm to the hinge mount plates of the bracket. Each hinge assembly comprises a hinge block adapted to be fastened in a fixed position relative to a hinge mount plate of the bracket and a hinge hub fastened to a leg of the swing arm. The hinge block has a cavity adapted to receive the hinge hub. The hinge block and hinge hub are coupled together for rotation relative to each other. A retainer, such as a torque insert, may be employed to couple the hinge block and hinge hub together. Torque inserts are, for example, offered by Reell Precision Manufacturing Corporation of St. Paul, Minnesota. Such torque inserts are adapted to eliminate nearly all the torque required to move the hinges in one direction without compromising the holding force in the other direction.

When the mount of the present invention is assembled, the swing arm is adapted to rotate between an open position wherein the connecting section of the swing arm is positioned at or above the top plate of the bracket, and a capture position, e.g., a position in which the parallel legs of the swing arm extend outwardly from the bracket generally perpendicular to the mounting plate and generally parallel to the top plate and bottom plate. The torque inserts of the hinges are adapted to require very little torque to rotate the swing arm from the open position to the capture position and to require significantly greater torque to rotate the swing arm from the capture position toward the open position. As such, when a case, duffel, backpack, or other container or items is position on the bottom plate and the swing arm is in the capture position, the case, duffel, backpack, other container, or item is securely held in place until someone applies sufficient torque to the swing arm to move the swing arm into the open position.

In alternative embodiments, the torque inserts can be replaced by pins serving as an axle with either detents to latch the hinge assemblies in, or biasing springs to bias the hinge assemblies toward, the capture position. The holding force of the detent or the biasing force of the spring should be sufficient to hold the swing arm in the capture position, while permitting a user to easily supply an opposing force sufficient to move the swing arm to the open position when either stowing or removing a case, duffel, or backpack. Also, padding may be applied to the bracket or swing arm cushion the case, duffel, or backpack.

BRIEF DESCRIPTION OF THE DRAWINGS

The foregoing features, objects and advantages of the invention will become apparent to those skilled in the art from the following detailed description of the preferred embodiment, especially when considered in conjunction with the accompanying drawings in which like numerals in the several views refer to corresponding parts.

DESCRIPTION OF THE PREFERRED EMBODIMENT

Figure 1:
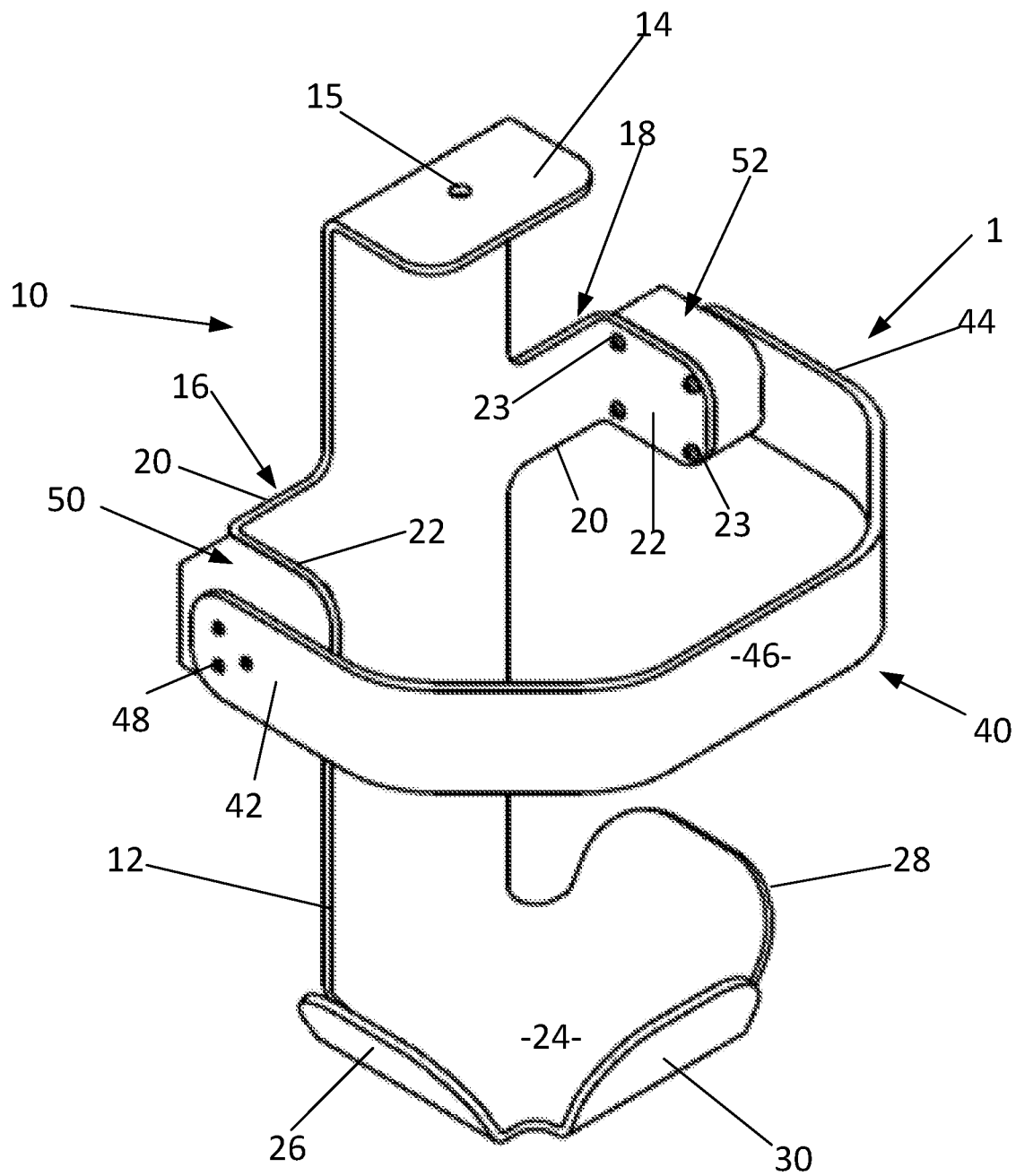
FIG. 1 is a perspective view of a mount made in accordance with the present invention.
Figure 2:
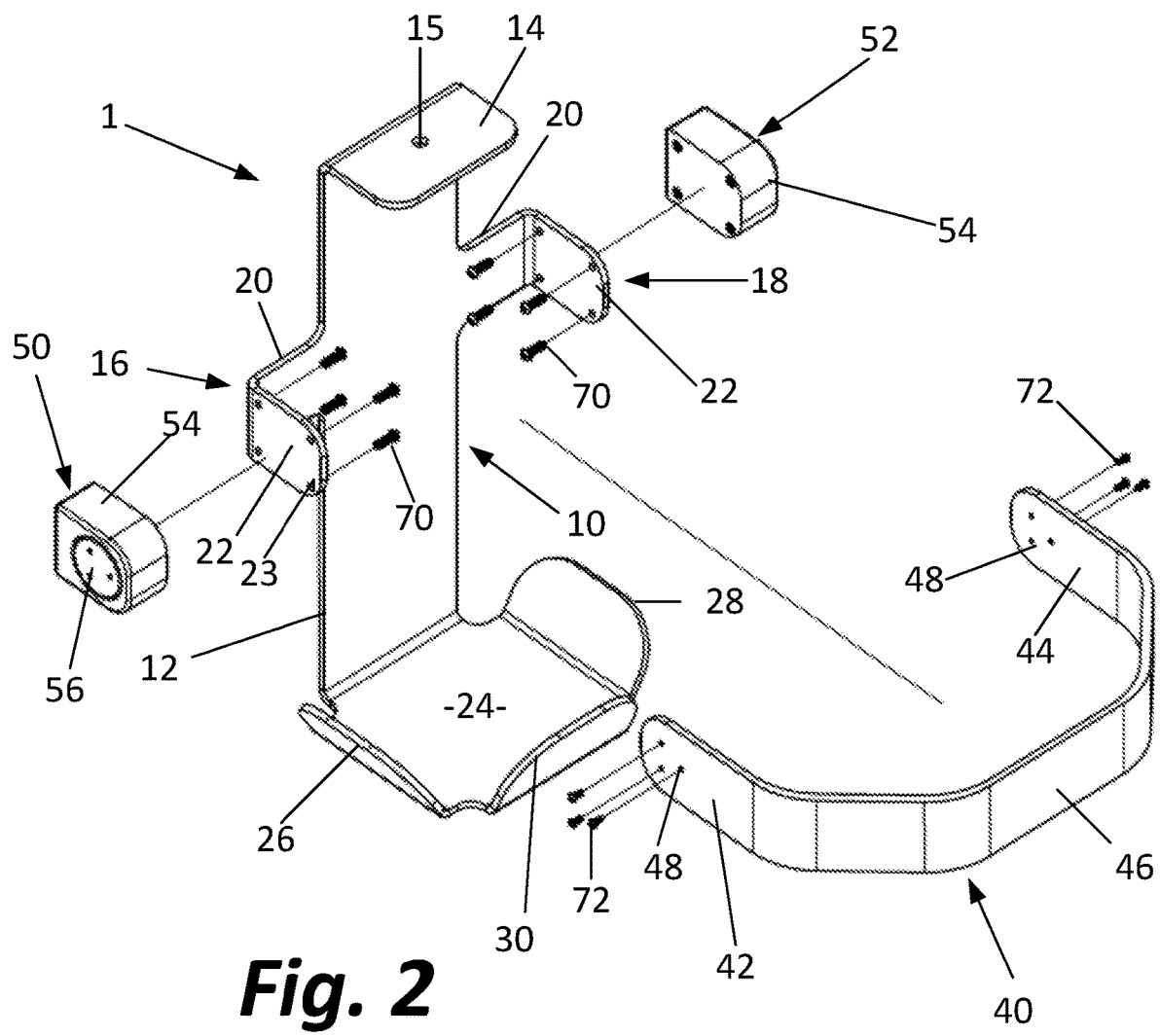
FIG. 2 is an exploded perspective view of the mount of FIG. 1.
Figure 3:
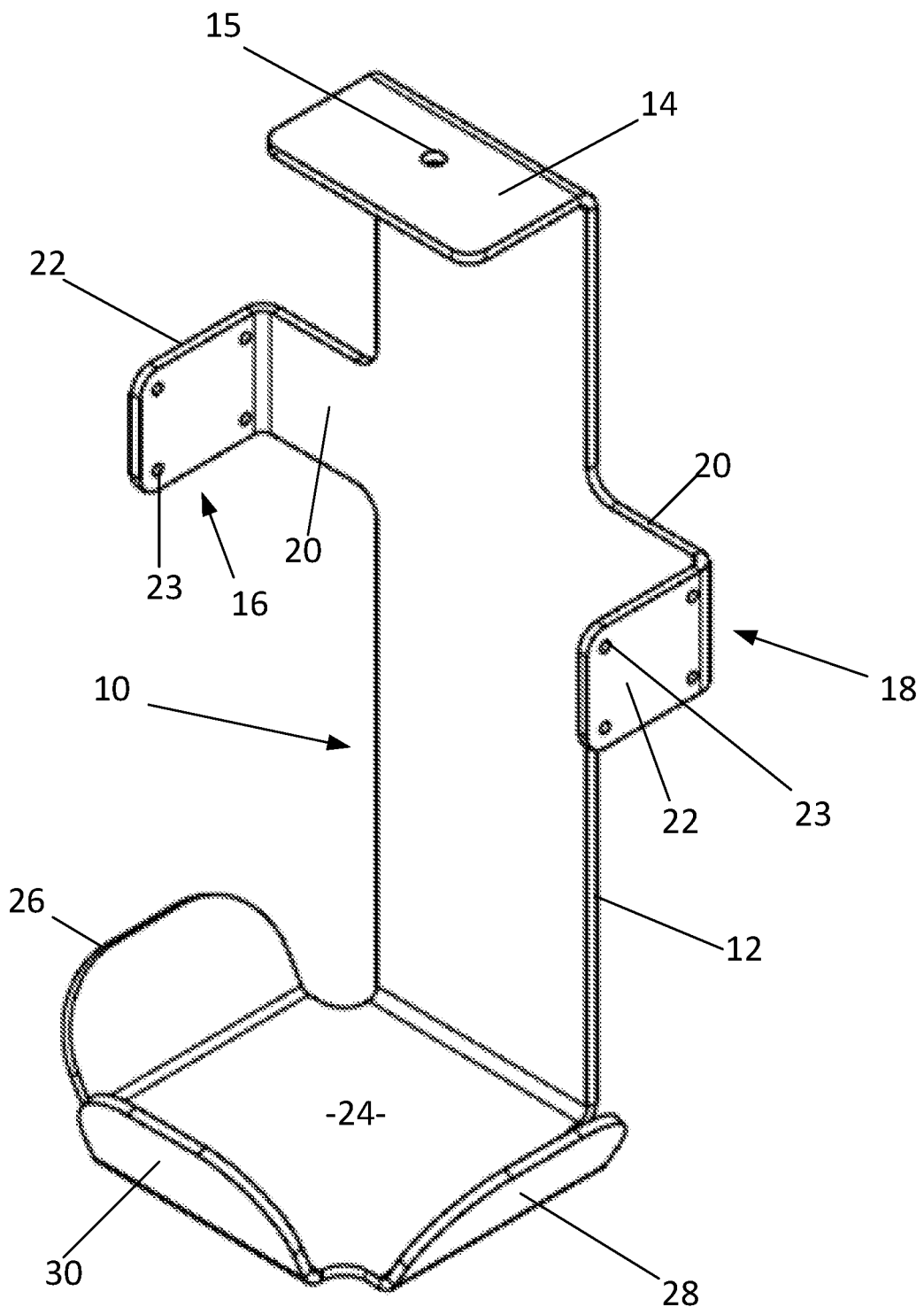
FIG. 3 is a perspective view of the bracket of the mount of FIG. 1.

This description of the preferred embodiments is intended to be read in connection with the accompanying drawings, which are to be considered part of the entire written description of this invention. In the description, relative terms such as "lower", "upper", "horizontal", "vertical", "above", "below", "up", "down", "top" and "bottom" as well as derivatives thereof (e.g., "horizontally", "downwardly", "upwardly", etc.) should be construed to refer to the orientation as then described or as shown in the drawings under discussion. These relative terms are for convenience of description and do not require that the apparatus be constructed or operated in a particular orientation. Terms such as "connected", "connecting", "attached", "attaching", "join" and "joining" are used interchangeably and refer to one structure or surface being secured to another structure or surface or integrally fabricated in one piece, unless expressly described otherwise.

The drawings show an illustrative embodiment of a mount used to temporarily secure an item such as a case, duffel, or backpack (none of which are shown) to a surface. Equipment could be contained within the case, duffel, or backpack, and the surface could be that of a cart, table, wall, or shelf such as those found in an ambulance or emergency medical services vehicle.

Figure 4:
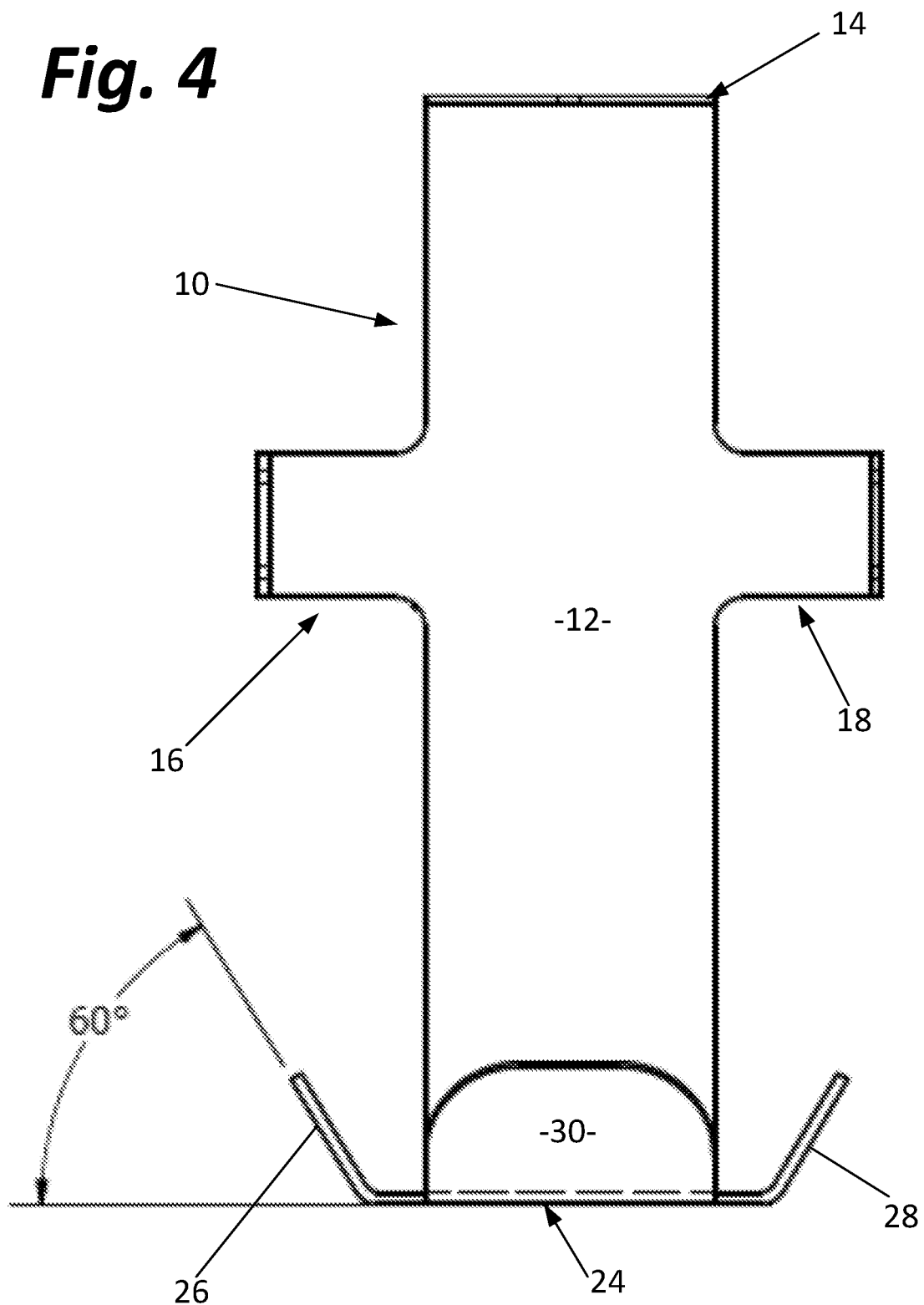
FIG. 4 is a front plan view of the bracket of FIG. 3.
Figure 5:
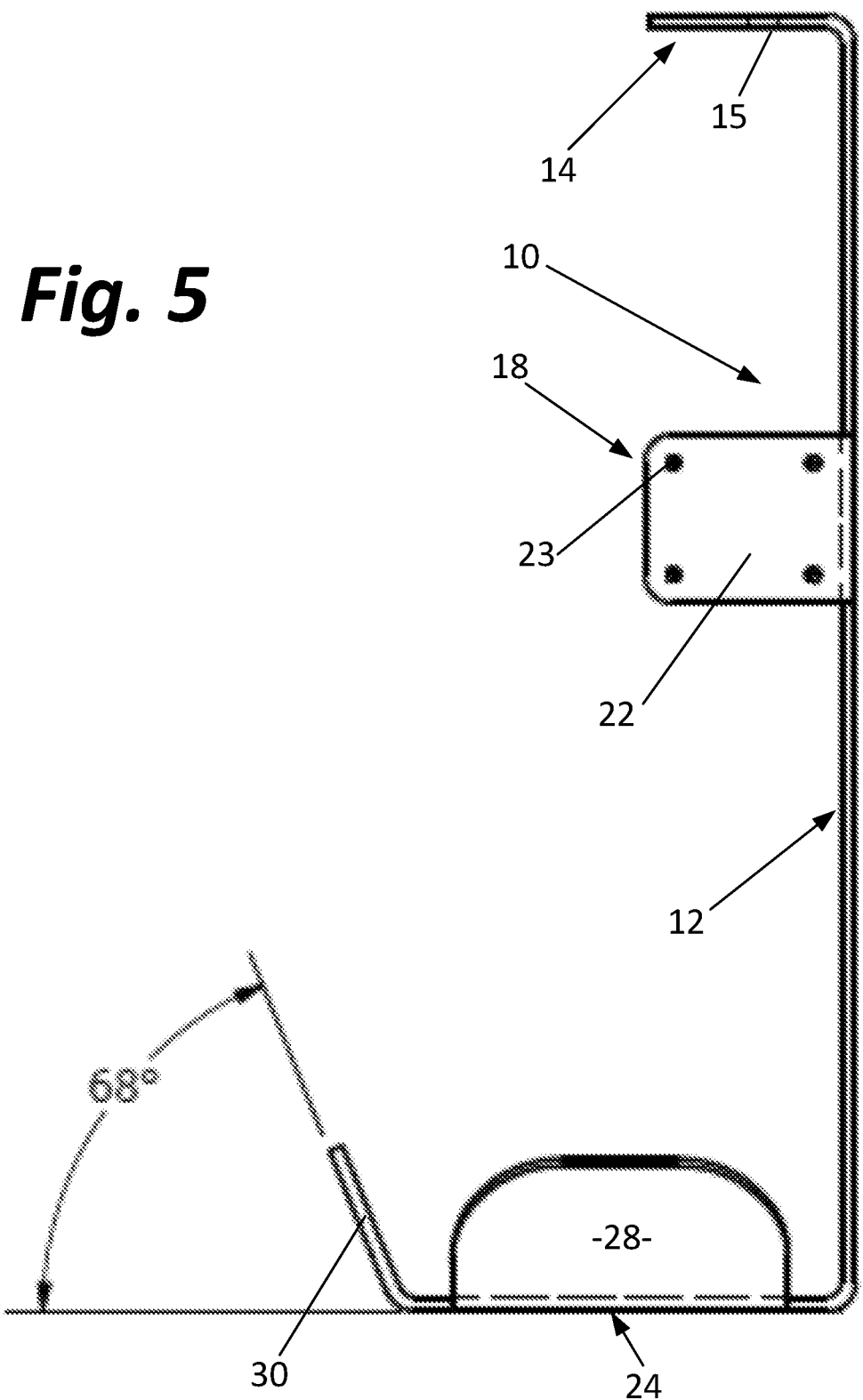
FIG. 5 is side plan view of the bracket of FIG. 3.

The mount 1 comprises a bracket 10 and a swing arm 40 adapted to be coupled to the bracket 10 by a pair of hinge assemblies 50 and 52. The bracket 10 includes a mounting plate 12 having a top section, a center section, and a bottom section. Extending outwardly from the top section is a top plate 14. A pair of arms 16 and 18 extend from the center section. Each arm 16/18 comprises a laterally extending plate 20, and an outwardly projecting hinge mount plate 22. Extending outwardly from the bottom section is a bottom plate 24. Capture plates 26, 28 and 30 extend upwardly from each of three free edges of the bottom plate, i.e., a front free edge and a pair of opposing side free edges, at an angle of greater than 90-degrees. FIG. 4 shows a labeled angle of 60-degrees which is supplementary to the angle between capture plate 26 and bottom plate 24. One with an understanding of basic geometry would therefore understand that the capture plates 26 and 28 extending from the free side edges of the bottom plate 24 at an angle of 120-degrees. Likewise, FIG. 5 shows a labeled angle of 68-degrees which is supplementary to the angle between capture plate 30 and bottom plate 24. One with an understanding of basic geometry would therefore understand that the capture 30 extends from the free front edge of the bottom plate 24 at an angle of 112-degrees. These angles may be modified without deviating from the invention.

The bracket 10 may be formed as a single piece of mold plastic or bent metal. Bracket mounting holes, only some of which are shown, may be provided through the mounting plate 12, top plate 14 or bottom plate 24. Exactly where these holes are positioned depends on how the mount 1 is to be coupled to, and oriented with respect to, the surface. Fasteners such as screws, nails, or bolts (also not shown) may be passed through these bracket mounting holes to couple the bracket 10 to a surface. For example, a screw may be passed through the mounting hole 15 extending through top plate 14 if one desires to fasten the mount 1 to the bottom of a shelf or other horizontal surface. Four hinge mounting holes 23 extend through each hinge mount plate 22.

Figure 6:
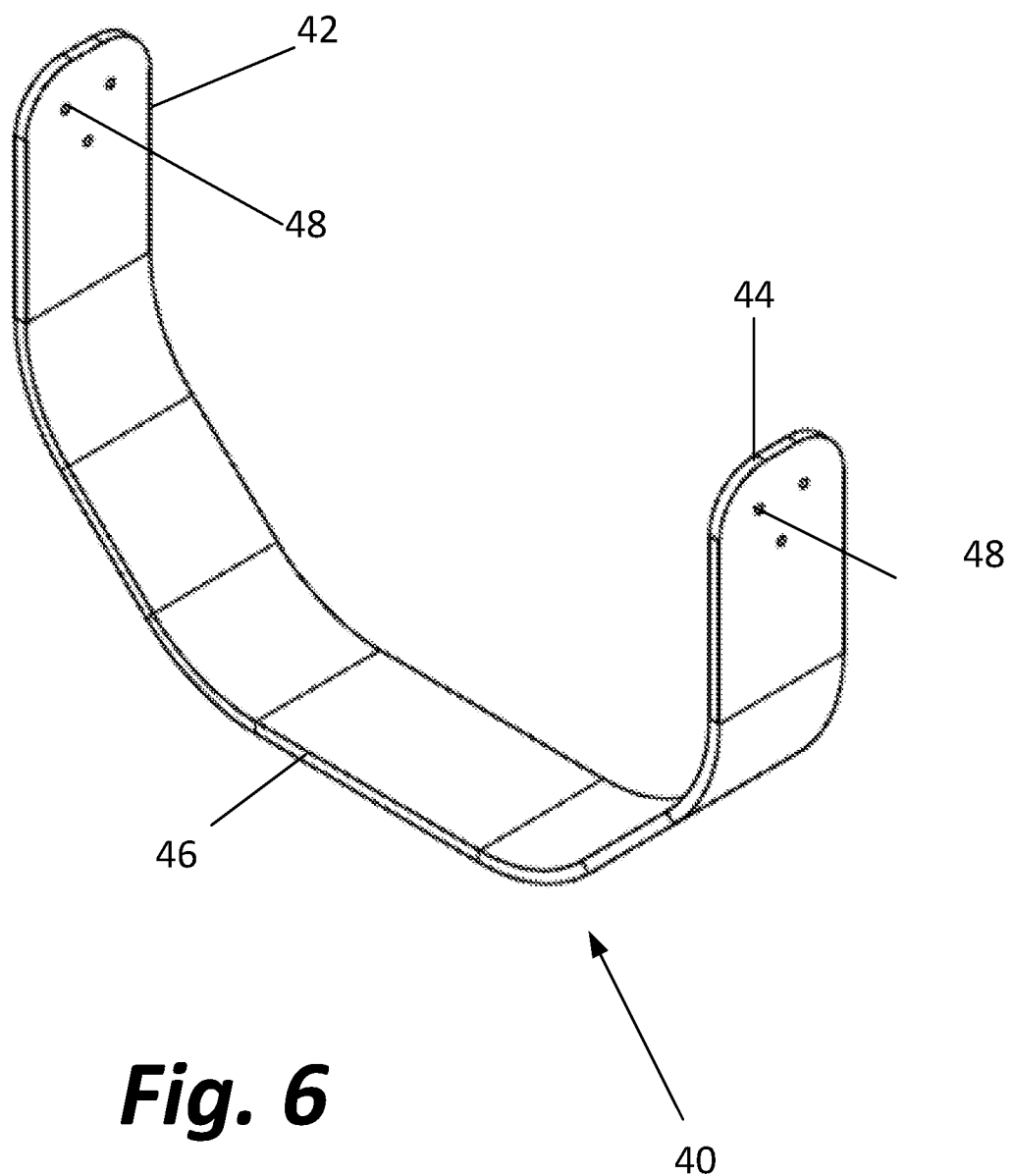
FIG. 6 is a perspective view of the swing arm of the mount of FIG. 1.
Figure 7:
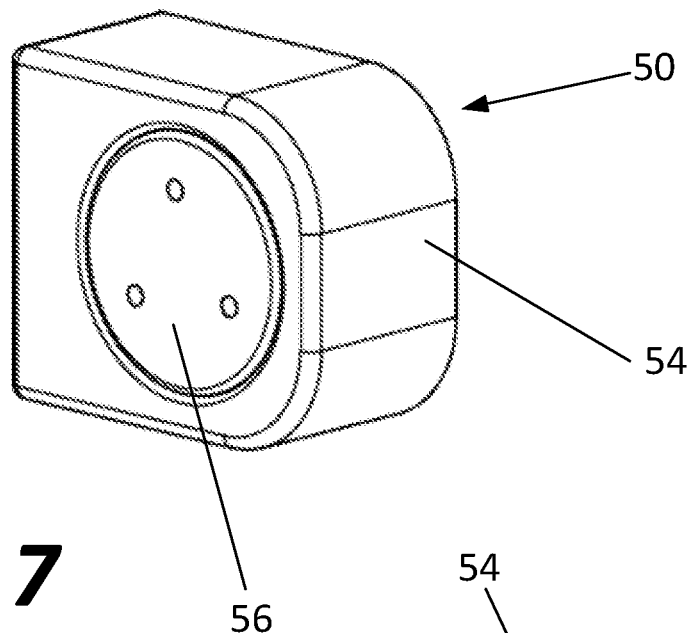
FIG. 7 is perspective view of one of the hinge assemblies of the mount of FIG. 1.
Figure 8:
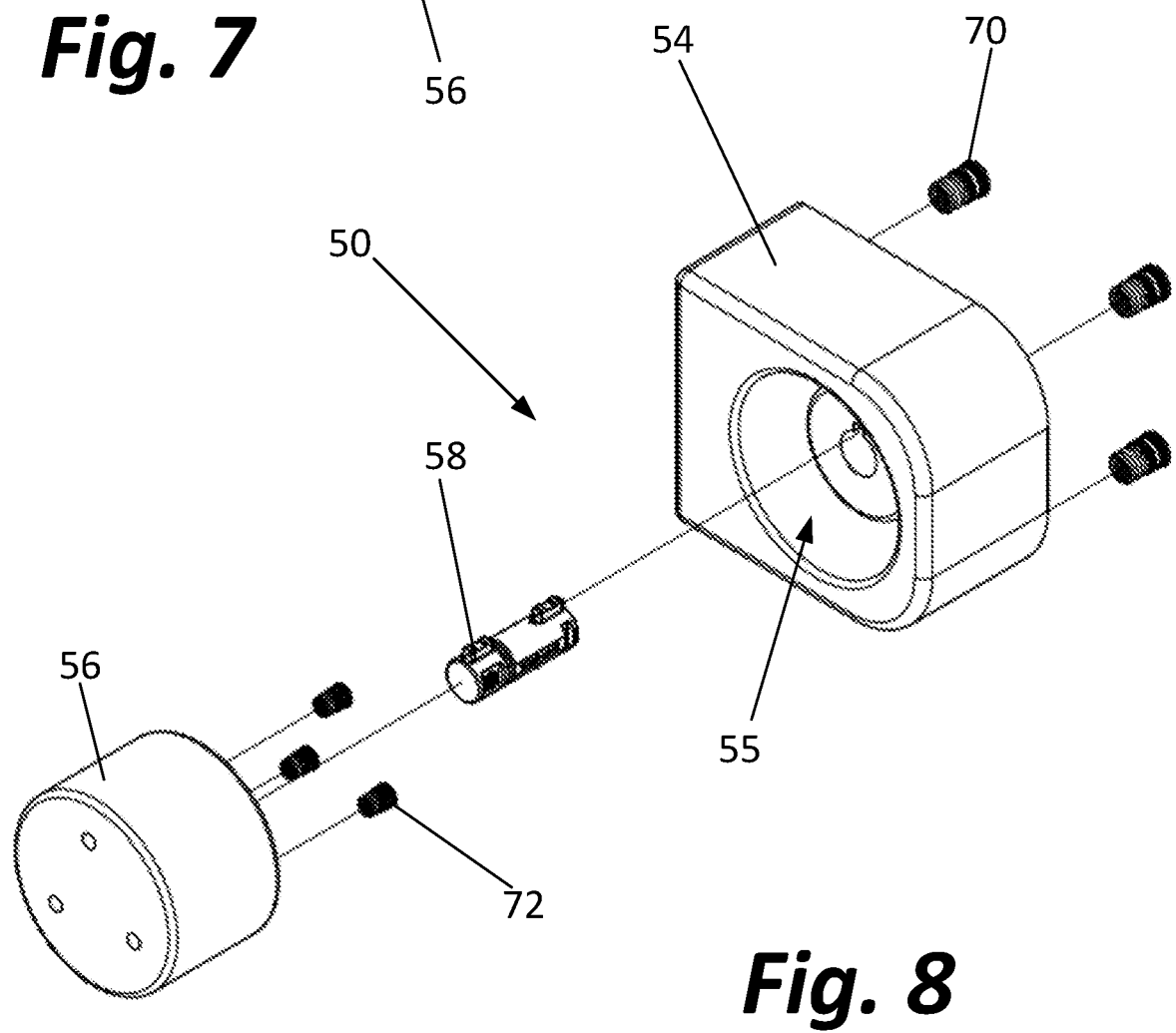
FIG. 8 is an exploded perspective view of the hinge assembly of FIG. 7.

The swing arm 40 is generally u-shaped having two parallel legs 42 and 44 and a connecting section 46 from which the two legs 42 and 44 extend. The connecting section 46 may be formed as a continuous curve or may comprise a series of flat subsections angled with respect to each other. The entire swing arm 40 may be formed as a single piece of molded plastic or bent metal. As shown in FIG. 6, each of the parallel legs 42 and 44 have three hinge coupling holes 48.

The hinge assemblies 50 and 52 are employed to rotatably couple the parallel legs 42/44 of the swing arm 40 to the hinge mount plates 22 of bracket 10. Each hinge assembly comprises a hinge block 54 adapted to be fastened, using screws 70, in a fixed position relative to a hinge mount plate 22 of the bracket 10 and a hinge hub 56 adapted to be fastened, using screws 72, to a leg 42/44 of the swing arm 40.

The hinge block 54 has a cavity 55 adapted to receive the hinge hub 56. The hinge block 54 and hinge hub 56 are coupled together for rotation relative to each other using a retainer such as a torque insert 58. Torque inserts are, for example, offered for sale by Reell Precision Manufacturing Corporation of St. Paul, Minnesota. Such torque inserts 58 are adapted to eliminate nearly all the torque required to move the hinge hubs 56 in one direction without compromising the holding force in the other direction.

When the mount 1 of the present invention is assembled, the swing arm 40 is adapted to rotate between an open position wherein the connecting section 46 of the swing arm 40 is positioned near or above the top plate 14 of bracket 10, and a capture position, e.g., a position in which the parallel legs 42 and 44 of the swing arm 40 extend outwardly from the bracket 10 generally perpendicular to the mounting plate 12 and generally parallel to the top plate 14 and bottom plate 24. The torque inserts 58 of the hinges are adapted to require very little torque to rotate the swing arm 40 from the open position to the capture position and to require significantly greater torque to rotate the swing arm 40 from the capture position toward the open position. As such, when a case, duffel or backpack is positioned adjacent the mounting plate 12, and between the top plate 14 and bottom plate 24, and the swing arm 40 is in the capture position, the case, duffel, or backpack is securely held in place by the mount 1 until someone applies sufficient torque to the swing arm 40 to move the swing arm 40 into the open position.

In alternative embodiments, the retainers of the hinges 50/52 may be assemblies comprising pins serving as an axle and detents to temporarily latch the hinges 50/52 and swing arm 40 in the capture position. In other alternative embodiments the retainers of the hinges 50/52 may be assemblies comprising pins serving as an axle and biasing springs adapted to bias the hinges 50/52 and swing arm 40 toward the capture position. The holding force of the detent or the biasing force of the spring should be sufficient to hold the swing arm 40 in the capture position, while permitting a user to easily supply sufficient torque to move the swing arm 40 to the open position to either stow or remove a case, duffel, or backpack. Also, padding may be applied to the bracket 10 or swing arm 40 to cushion the case, duffel, or backpack.

This invention has been described herein in considerable detail to comply with the patent statutes and to provide those skilled in the art with the information needed to apply the novel principles and to construct and use embodiments of the example as required. However, it is to be understood that the invention can be carried out by specifically different devices and that various modifications can be accomplished without departing from the scope of the invention itself.

What is claimed is:

1. A mount for supporting a container, comprising a bracket comprising a mounting plate, a top plate, a bottom plate, and a pair of arms, each of said arms comprising an outwardly projecting hinge mount plate, (b) a swing arm comprising a connecting section and two parallel legs each extending from the connection section at a fixed angle relative to the connecting section, (c) a first hinge assembly rotatably coupling a first of the two parallel legs of the swing arm to the bracket, and (d) a second hinge assembly rotatably coupling a second of the two parallel legs of the swing arm to the bracket, wherein said first and second hinge assemblies are adapted to permit rotation of the swing arm between an open position and a capture position, and wherein each of said first and second hinge assemblies comprises a hinge hub and a hinge block adapted to receive the hinge hub, and at least one of said first and second hinge assembles further comprises a retainer adapted to retain the swing arm in the capture position until sufficient torque is applied to cause the swing arm to move from the capture position to the open position.

2. The mount of claim 1 wherein said retainer is a torque insert.

3. The mount of claim 1 wherein the pair of hinge assemblies connect the outwardly projecting hinge mount plates of pair of arms of the bracket to the two parallel legs of the swing arm.

4. The mount of claim 3 wherein the hinge hubs are connected to the legs of the swing arm and the hinge blocks are connected to the outwardly projecting hinge mount plates of the bracket.

5. The mount of claim 1 wherein said bracket further comprises at least one capture plate extending upwardly from the bottom plate.

6. The mount of claim 1 wherein said bottom plate comprises a front free edge and a pair of opposing side free edges, and wherein capture plates extend upwardly from the front free edge and each of the pair of opposing side free edges of the bottom plate at an angle from the bottom plate greater than 90-degrees.

7. The mount of claim 1 wherein said bottom plate comprises first and second opposing side free edges, a first capture plate extending upwardly from said first opposing side free edge at an angle of 60-degrees from the bottom plate, and a second capture plate extending upwardly from said second opposing side free edge at an angle of 60-degrees from the bottom plate.

8. The mount of claim 7 wherein said bottom plate further comprises a front free edge, and a third capture plate extending upwardly from the front free edge at an angle of 68-degrees from the bottom plate.

9. A mount for supporting a container, comprising a bracket having a mounting plate, a top plate, a bottom plate, and a pair of arms, each of said arms comprising an outwardly projecting hinge mount plate, a swing arm comprising a connecting section and two parallel legs each extending from the connection section at a fixed angle relative to the connecting section, a first hinge assembly rotatably coupling a first of the two parallel legs of the swing arm to a first of the pair of arms of the bracket, and a second hinge assembly rotatably coupling a second of the two parallel legs of the swing arm to a second of the pair of arms of the bracket, said first and second hinge assemblies adapted to permit rotation of the swing arm between an open position and a capture position, each of said first and second hinge assemblies comprising a hinge hub and a hinge block adapted to receive the hinge hub, and at least one of said first and second hinge assemblies further comprising a torque insert adapted to retain the swing arm in the capture position until sufficient torque is applied to the swing arm to cause the swing arm to move from the capture position to the open position.

10. A mount for supporting a container, comprising:
    (a) a bracket comprising a mounting plate having a top section, a center section, and a bottom section, top plate extending from the top section, a bottom plate extending outwardly from the bottom section, at least one capture plate, and a pair of arms extending from the center section, wherein each arm of said pair of said arms comprises a laterally extending plate and an outwardly projecting hinge mount plate, and wherein said bottom plate has at least one free edge, and said at least one capture plate extends upwardly from said bottom plate at an angle of greater than 90-degrees from the bottom plate;
    (b) a swing arm having two parallel legs and a connecting section from which the two parallel legs extend at a fixed angle relative to the connecting section; and
    (c) a pair of hinge assembles adapted to couple the two parallel legs of the swing arm to the outwardly projecting hinge mount plates of the pair of arms of the bracket and permit rotation of the swing arm relative to the bracket between an open position and a capture position, each of said hinge assemblies comprising a hinge hub and a hinge block adapted to receive the hinge hub, and at least one of the hinge assemblies further comprising a torque insert adapted to retain the swing arm in the capture position until sufficient torque is applied to cause the swing arm to move from the capture position to the open position.

\* \* \* \* \*